United States Patent
Xia et al.

(10) Patent No.: US 8,987,521 B2
(45) Date of Patent: Mar. 24, 2015

(54) METHOD FOR PREPARING POLYOXYMETHYLENE DIMETHYL ETHERS BY ACETALATION REACTION OF FORMALDEHYDE WITH METHANOL

(75) Inventors: Chungu Xia, Gansu (CN); Heyuan Song, Gansu (CN); Jing Chen, Gansu (CN); Zhen Li, Gansu (CN)

(73) Assignee: Lanzhou Institute of Chemical Physics, Chinese Academy of Sciences, Gansu (CN)

( * ) Notice: Subject to any disclaimer, the term of this patent is extended or adjusted under 35 U.S.C. 154(b) by 561 days.

(21) Appl. No.: 13/164,677

(22) Filed: Jun. 20, 2011

(65) Prior Publication Data

US 2011/0313202 A1    Dec. 22, 2011

Related U.S. Application Data

(63) Continuation-in-part of application No. PCT/CN2011/072420, filed on Apr. 2, 2011.

(30) Foreign Application Priority Data

May 18, 2010 (CN) .......................... 2010 1 0176630

(51) Int. Cl.
  *C07C 41/14* (2006.01)
  *C07C 41/56* (2006.01)
  *C07C 41/58* (2006.01)

(52) U.S. Cl.
  CPC ................. *C07C 41/56* (2013.01); *C07C 41/58* (2013.01)
  USPC ....................................................... 568/601

(58) Field of Classification Search
  CPC ............................... C07C 41/56; C07C 41/58
  USPC ....................................................... 568/601
  See application file for complete search history.

(56) References Cited

U.S. PATENT DOCUMENTS

| 5,962,702 A | 10/1999 | Morishita | |
|---|---|---|---|
| 2008/0207954 A1* | 8/2008 | Stroefer et al. | 568/600 |
| 2008/0293954 A1* | 11/2008 | Chen et al. | 549/368 |
| 2009/0036715 A1* | 2/2009 | Chen et al. | 568/594 |

FOREIGN PATENT DOCUMENTS

| CA | 2581502 A1 | 5/2006 |
|---|---|---|
| CN | 101182367 A | 5/2008 |
| CN | 101665414 A | 3/2010 |
| EP | 1070755 A1 | 1/2001 |
| EP | 1505049 A1 | 2/2005 |
| WO | WO 2006045506 A1 | 5/2006 |

OTHER PUBLICATIONS

International Search Report and Written Opinion issued on Jul. 7, 2011 for International Patent Application No. PCT/CN2011/072377.

* cited by examiner

*Primary Examiner* — Rosalynd Keys
(74) *Attorney, Agent, or Firm* — Knobbe, Martens, Olson & Bear, LLP

(57) ABSTRACT

It is disclosed a method for preparing polyoxymethylene dimethyl ethers by continuous polymerization and acetalation reactions. The method may include two steps: performing a polymerization reaction of an aqueous formaldehyde solution under catalysis of an ionic liquid IL I to obtain a mixed aqueous solution of trioxymethylene and formaldehyde; and an acetalation reaction of the mixed aqueous solution of trioxymethylene and formaldehyde with methanol is performed under catalysis of an ionic liquid IL II to prepare polyoxymethylene dimethyl ethers. The method may use an aqueous formaldehyde solution as a starting material to prepare polyoxymethylene dimethyl ethers by continuous polymerization and acetalation reactions, achieving a high use ratio of formaldehyde. A film evaporator is used in the invention, realizing a rapid separation and recycling of the light components, with a high separation efficiency. The separation of the catalyst is simple, thereby realizing recycling of the catalyst.

21 Claims, 1 Drawing Sheet

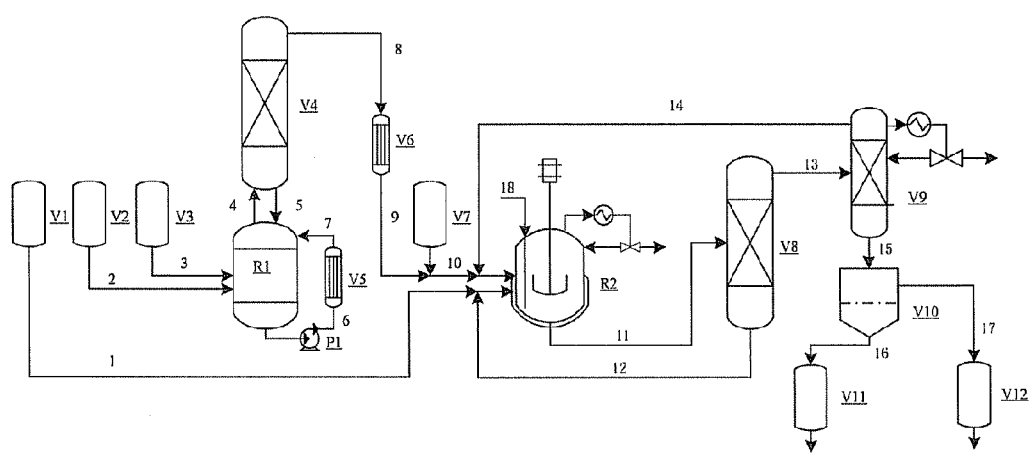

METHOD FOR PREPARING POLYOXYMETHYLENE DIMETHYL ETHERS BY ACETALATION REACTION OF FORMALDEHYDE WITH METHANOL

TECHNICAL FIELD

The present invention relates to a method for preparing polyoxymethylene dimethyl ethers ($H_3CO(CH_2O)_nCH_3$, $DMM_n$, n=2-6) by continuous polymerization and acetalation reactions using an aqueous formaldehyde solution as a starting material.

BACKGROUND ART

At the end of the $19^{th}$ century, with continuing renovations of internal-combustion engines, the improvement on oils has also drawn wide attentions. Being an organic fuel with a low price, diesel oil has the advantages of high thermal efficiency, low oil consumption, less discharge etc., and thus, it has become a trend to utilize diesel oil in internal-combustion engines. Additionally, because the molecular weights of the alkane components in diesel oil are relatively high, the burning rate of diesel oil during the operation of internal-combustion engines is not high enough and the burning performance thereof is not good enough, which not only increases the oil consumption, but also aggravates the degree of pollution of the discharged gases to the air. Thus, it is necessary to increase the burning performance of diesel oil in engines. In recent years, oxygen-containing fuels such as methanol, methylal or the like have been added into diesel oil, which effectively decreases the discharge of carbon smoke and exhaust gas. However, these compounds have low vapor pressure and cetane number, or poor solubility with diesel oil.

In 1998, the research of David S. Moulton (U.S. Pat. No. 5,746,785) indicated that, being a novel oil additive, polyoxymethylene dialkyl ethers ($RO(CH_2O)_nR$) can improve the burning characteristic of diesel oil remarkably, increase the thermal efficiency effectively, and reduce the discharge of $NO_x$ and carbon smoke greatly. Furthermore, they have very high cetane number and oxygen content, as well as good mutual solubility with common diesel oils, and therefore are regarded as an environmentally acceptable blending component for diesel oils with a promising application prospect.

In the earlier time, polyoxymethylene dialkyl ethers are prepared by the reaction of methanol with paraformaldehyde or glycol ethylidene-formal under the catalysis of a protonic acid, wherein the reaction temperature is between 150 to 180° C. and a byproduct of $CO_2$ is produced synchronously. In 1948, Du Pont (U.S. Pat. No. 2,449,469) investigated the acetalation reaction of polyoxymethylene ether with paraformaldehyde or concentrated formaldehyde using an inorganic acidic catalyst such as sulfuric acid under a relatively mild condition, which mainly produced polyoxymethylene dialkyl ethers wherein n=2-3.

In 2008, BASF (US 20080207954) reported a process for preparing $DMM_{3-4}$ by the reaction of methanol with an aqueous formaldehyde solution using a liquid acid or a solid acid as catalyst. This reaction process included an acetalation reactor, a reactive distillator and a phase separator. An acetalation reaction was performed between methanol and an aqueous formaldehyde solution in the reactor to produce $DMM_{1-4}$. Then, the crude products ($DMM_{1-4}$, starting materials, and water) and the catalyst solution (the catalyst and the high boiling compounds) were separated by using a reactive distillation, and the catalyst solution was recycled for reuse. After being removed of $DMM_1$ and a part of the reaction starting materials by distillation, the crude products then entered the phase separator for removing water by separation so as to obtain a product of $DMM_{3-4}$. Taking an aqueous formaldehyde solution as the reaction starting material directly led to a low yield of product, a complex separation process and high energy consumption.

BP Company developed heterogeneous catalyst systems of borosilicate molecular sieve, sulfonic acid-based cation exchange resin or the like (U.S. Pat. Nos. 5,959,156, 6,160,174, 6,2655,284). Dimethyl ether and methanol were used as the starting materials to produce formaldehyde via a hydration reaction of dimethyl ether. Further, an acetalation reaction of formaldehyde and methanol produced $DMM_n$. In this reaction process, the separation of the products ($DMM_{\geq 2}$) and the reuse of the starting materials were realized in a reactive rectification manner. However, the catalyst in this method had a low activity and had to be regenerated frequently, leading to a complex process.

In recent years, Lanzhou Institute of Chemical Physics, Chinese Academy of Sciences (U.S. Pat. No. 7,560,599 B2) reported a method for synthesizing $DMM_n$ by an acetalation reaction of methanol with trioxymethylene catalyzed by an ionic liquid, wherein the reaction conversion could be up to 90% and the selectivity for $DMM_{3-8}$ could be up to 40%. The separation and recycling of the catalyst were realized (CN 200810150868.4).

SUMMARY OF INVENTION

An object of the invention is to provide a method for preparing polyoxymethylene dimethyl ethers ($H_3CO(CH_2O)_nCH_3$, $DMM_n$, n=2-6) by continuous reactions of polymerization and acetalation using an aqueous formaldehyde solution as a starting material.

The method of the invention includes two steps: firstly, performing a polymerization reaction of formaldehyde (a 50-60 wt % aqueous solution) under catalysis of an ionic liquid IL I to obtain a mixed aqueous solution of trioxymethylene and formaldehyde; and then an acetalation reaction of the mixed aqueous solution of trioxymethylene and formaldehyde with methanol is performed under catalysis of an ionic liquid IL II to prepare polyoxymethylene dimethyl ethers.

In the invention, firstly, a polymerization reaction is carried out in a reaction-rectification device in the presence of an ionic liquid IL I catalyst by using formaldehyde (a 50-60 wt % aqueous solution) as a starting material to obtain a mixture of trioxymethylene and formaldehyde. Then, an acetalation reaction of the mixture of trioxymethylene and formaldehyde with methanol is performed under catalysis of an ionic liquid IL II in a tank reactor to prepare $DMM_n$. The reaction liquid is separated into a light component a1 (formaldehyde, methanol, trioxymethylene, $DMM_{1-6}$ and water) and a recycling catalyst (the ionic liquids and $DMM_{>6}$) by rectification. Subsequently, a1 is separated into a light component b1 ($DMM_{1-2}$, formaldehyde, methanol, trioxymethylene and a part of water), products ($DMM_{3-6}$) and water by using a combined separating method of film evaporation and phase separation. The light component b1 and the catalyst are recycled to the reactor to proceed with the catalysis reaction.

The reaction formulas of the invention are:
the first step of producing trioxymethylene by polymerization of formaldehyde:

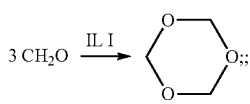

the second step of preparing DMM$_n$ by acetalation reaction:

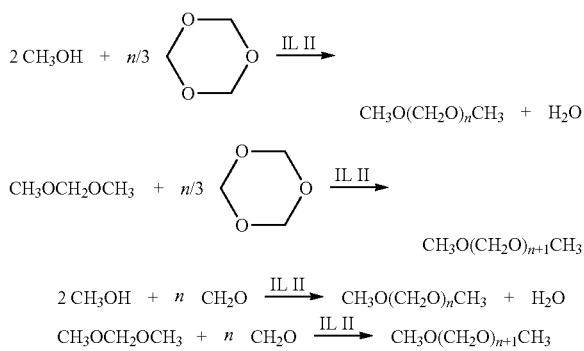

wherein n is an integer of 1-6.

The invention provides a method for preparing polyoxymethylene dimethyl ethers by acetalation reaction of formaldehyde and methanol, including steps of:

A, in a formaldehyde polymerization reaction-rectification zone including a reaction-rectification device and a gas condenser, carrying out a continuous polymerization reaction by using an acidic ionic liquid IL I as a catalyst and an aqueous formaldehyde solution as a starting material, and passing the polymerization product through the rectification device and the gas condenser;

B, in an acetalation reaction zone, in a single-stage or multi-stage stirred tank reactor, performing a continuous acetalation reaction between the condensate from the gas condenser in step A and methanol by using an acidic ionic liquid IL II as a catalyst;

C, in a separation zone including a single-stage or multi-stage rectification tower, a film evaporator and a phase separator connected in series, allowing the reactor effluent from the above acetalation reaction zone to drop in pressure, and flow into the rectification tower to be evaporated and condensed so as to be separated into two streams, one of a gaseous light component a1 and one of a liquid recycling catalyst; directing the recycling catalyst back to the acetalation reactor; allowing the light component a1 to flow into the film evaporator to be separated into a gaseous light component b1 and a liquid phase; and allowing the separated liquid phase to flow into the phase separator to be separated into two streams, one of a product phase and one of an aqueous phase.

The method of the invention is characterized in that in step A, the aqueous formaldehyde solution as the starting material is 50-60 wt %.

The method of the invention is characterized in that in step A, the polymerization reaction in the formaldehyde polymerization reaction-rectification zone is carried out at 80-120° C. and −1.0-0.1 MPa.

The method of the invention is characterized in that the acidic ionic liquid IL I used in step A has a cation portion which is at least one selected from the group consisting of cations of quaternary ammoniums, cations of quaternary phosphines, cations of imidazoles, cations of pyridines and cations of heterocycles, and an anion portion which is at least one selected from the group consisting of p-toluenesulfonate, trifluoromethyl sulfonate, methyl sulfonate, hydrosulfate, and trifluoroacetate.

The method of the invention is characterized in that in step B, the acetalation reaction is carried out at 100-130° C. and 0.5-5.0 MPa.

The method of the invention is characterized in that the acidic ionic liquid IL II used in step B has a cation portion which is at least one selected from the group consisting of cations of quaternary ammoniums, cations of quaternary phosphines, cations of imidazoles, cations of pyridines and cations of heterocycles, and an anion portion which is at least one selected from the group consisting of p-toluenesulfonate, trifluoromethyl sulfonate, methyl sulfonate, methoxy sulfonate, hydrosulfate, and trifluoroacetate.

The method of the invention is characterized in that in step C, the treatment in the rectification tower is carried out under a protection of nitrogen gas.

The method of the invention is characterized in that in step C, the treatment in the film evaporator is carried out under a protection of nitrogen gas.

The method of the invention is characterized in that the acidic ionic liquid IL I used in step A has a cation portion selected from cations of imidazoles, and an anion portion selected from toluenesulfonate, trifluoromethyl sulfonate and hydrosulfate.

The method of the invention is characterized in that in the formaldehyde polymerization reaction-rectification zone in step A, the catalyst of acidic ionic liquid IL I accounts for 1-10 wt % of all the starting materials.

The method of the invention is characterized in that in the formaldehyde polymerization reaction-rectification zone in step A, the reaction temperature is 95-105° C.; the pressure is −0.1 MPa-0.1 MPa; and the residence time of the reaction is 5-15 h.

The method of the invention is characterized in that in the formaldehyde polymerization reaction-rectification zone in step A, the rectification tower has a bottom temperature of 90-98° C. and a overhead temperature of 92-96° C.; the rectification tower is packed with a structured packing of stainless steel and has a tray number of 10-20; and the material of the reactor is 316L stainless steel.

The method of the invention is characterized in that in the acetalation reaction zone in step B, the starting material which is the condensate from the gas condenser in step A is a mixture of trioxymethylene, formaldehyde and water, wherein the ratio of the total moles of formaldehyde and trioxymethylene to the moles of methanol which is another starting material is 0.9-3.0.

The method of the invention is characterized in that in step B, the acidic ionic liquid IL II has a cation portion selected from cations of imidazoles, and an anion portion selected from methoxy sulfonate or hydrosulfate.

The method of the invention is characterized in that in the acetalation reaction zone in step B, the catalyst of acidic ionic liquid IL II accounts for 1-5 wt % of all the starting materials.

The method of the invention is characterized in that in the acetalation reaction zone in step B, the reaction temperature is preferably 115-120° C.; the reaction system is charged with an inert gas, preferably nitrogen gas or helium gas, with a pressure of 1.0-3.0 MPa; the residence time of the reaction is 20-60 min; and the material of the reactor is 316L stainless steel.

The method of the invention is characterized in that in the separation zone in step C, the rectification tower is packed with a structured packing of stainless steel and has a tray number of 10-20, a pressure of −0.02--0.06 MPa and an overhead temperature of 20-260° C.

The method of the invention is characterized in that in the separation zone in step C, the film evaporator is selected from a falling film evaporator, a scraper thin film evaporator and a scraper-less thin film evaporator, and the operating conditions thereof include an evaporation temperature of 20-100° C. and a pressure of −0.1--0.01 MPa.

The invention provides a method for preparing polyoxymethylene dimethyl ethers by acetalation reaction of formaldehyde and methanol, including steps of:

A, in a formaldehyde polymerization reaction-rectification zone including a reaction-rectification device and a gas condenser, carrying out a continuous polymerization reaction by using an acidic ionic liquid IL I as a catalyst and a 50-60 wt % aqueous formaldehyde solution as a starting material at 80-120° C. and −1.0-0.1 MPa to produce trioxymethylene; the gas discharged from the reaction-rectification device is an azeotrope of trioxymethylene, formaldehyde and water, which contains 30-40 wt % of trioxymethylene and 10-30 wt % of formaldehyde; the gas is collected and directed to a gas condenser V6, and after condensation enters an acetalation reactor R2; wherein the acidic ionic liquid IL I has a cation portion which is at least one selected from the group consisting of cations of quaternary ammoniums, cations of quaternary phosphines, cations of imidazoles, cations of pyridines and cations of heterocycles, and an anion portion which is at least one selected from the group consisting of p-toluenesulfonate, trifluoromethyl sulfonate, methyl sulfonate, hydrosulfate, and trifluoroacetate;

B, in an acetalation reaction zone, in a single-stage or multi-stage stirred tank reactor, a continuous acetalation reaction is performed between the condensed mixture of trioxymethylene, formaldehyde and water from step A and methanol by using an acidic ionic liquid IL II as a catalyst at 100-130° C. and under 0.5-5.0 MPa; the reactor effluent eluted continuously from the reaction zone, in addition to the $DMM_{1-6}$ and water produced, further comprises unreacted starting materials and the catalyst; the acidic ionic liquid IL II has a cation portion which is at least one selected from the group consisting of cations of quaternary ammoniums, cations of quaternary phosphines, cations of imidazoles, cations of pyridines and cations of heterocycles, and an anion portion which is at least one selected from the group consisting of p-toluenesulfonate, trifluoromethyl sulfonate, methyl sulfonate, methoxy sulfonate, hydrosulfate, and trifluoroacetate;

C, in a separation zone including a single-stage or multi-stage rectification tower, a film evaporator and a phase separator connected in series, allowing the reactor effluent from the above acetalation reaction zone to drop in pressure, and flow continuously into the rectification tower to be evaporated and condensed under a protection of nitrogen gas so as to be separated into two streams, one of a light component a1 and one of a recycling catalyst, wherein the light component a1 comprises formaldehyde, methanol, trioxymethylene, $DMM_{1-6}$ and water; directing the recycling catalyst back to the acetalation reactor; allowing the light component a1 to flow continuously into the film evaporator to be evaporated and condensed under a protection of nitrogen so as to be separated into a light component b1 and a liquid phase, wherein the light component b1 comprises $DMM_{1-2}$, formaldehyde, methanol, trioxymethylene and a part of water, and the separated liquid phase comprises a mixed solution of $DMM_{3-6}$ and water; and allowing the liquid phase to flow continuously into the phase separator to be separated into two streams, one of a product phase and one of an aqueous phase, where the product mainly comprises $DMM_{3-6}$.

In the formaldehyde polymerization reaction-rectification zone, the acidic ionic liquid IL I preferably has a cation portion selected from cations of imidazoles, and an anion portion selected from toluenesulfonate, trifluoromethyl sulfonate or hydrosulfate.

In the formaldehyde polymerization reaction-rectification zone, the catalyst of acidic ionic liquid IL I accounts for 1-10 wt % of all the starting materials.

Examples of the ionic liquid IL I have cations of the following structural formulas:

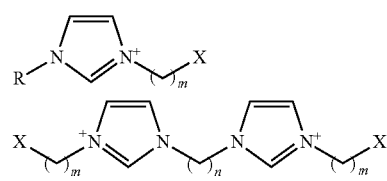

wherein, n and m are integers of 0-15; R is a straight-chain alkyl with carbon number of 1-6 or a benzene ring; and X is —$SO_3H$ or —COOH.

Examples of the ionic liquid IL I have anions of the following structural formulas:

$$CH_3PhSO_3^-, CF_3SO_3^-, HSO_4^-.$$

In the formaldehyde polymerization reaction-rectification zone, the reaction temperature is preferably 95-105° C.; the pressure is −0.1 MPa-0.1 MPa; and the residence time of the reaction is 5-15 h.

In the formaldehyde polymerization reaction-rectification zone, the rectification tower has a bottom temperature of 90-98° C. and a overhead temperature of 92-96° C.; the rectification tower is packed with a structured packing of stainless steel and has a tray number of 10-20; and the material of the reactor is 316L stainless steel.

In the acetalation reaction zone, the starting materials are trioxymethylene, formaldehyde and methanol, wherein the ratio of the total moles of formaldehyde and trioxymethylene to the moles of methanol is 0.9-3.0. The acidic ionic liquid IL II preferably has a cation portion selected from cations of imidazoles, and an anion portion selected from methoxy sulfonate or hydrosulfate.

In the acetalation reaction zone, the catalyst of acidic ionic liquid IL II accounts for 1-5 wt % of all the starting materials.

Examples of the ionic liquid IL II have cations of the following structural formulas:

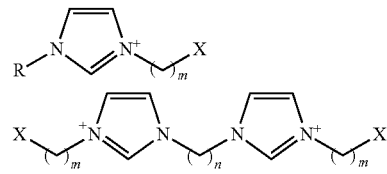

wherein, n and m are integers of 0-15; R is a straight-chain alkyl with carbon number of 1-6 or a benzene ring; and X is —$SO_3H$, —COOH or —$SO_3R'$, where R' is $CH_3$ or $CH_2CH_3$.

Examples of the ionic liquid IL II have anions of the following structural formulas:

$$CH_3OSO_3^-, CH_3SO_3^-, HSO_4^-.$$

In the acetalation reaction zone, the reaction temperature is preferably 115-120° C.; the reaction system is charged with an inert gas, preferably nitrogen gas or helium gas, with a preferable pressure of 1.0-3.0 MPa; the residence time of the reaction is 20-60 min; and the material of the reactor is 316L stainless steel.

In a separation zone, the rectification tower is packed with a structured packing of stainless steel and has a tray number of 10-20, a pressure of −0.02−−0.06 MPa and an overhead temperature of 20-260° C.; the film evaporation device is selected from a falling film evaporator, a scraper thin film evaporator and a scraper-less thin film evaporator, and the operating conditions thereof include an evaporation temperature of 20-100° C. and a pressure of −0.1−−0.01 MPa.

The invention has the following advantages:

1. The invention uses an aqueous formaldehyde solution as a starting material to prepare polyoxymethylene dimethyl ethers by continuous polymerization and acetalation reactions, achieving a high use ratio of formaldehyde.

2. A film evaporator is used in the invention, realizing a rapid separation and recycling of the light components ($DMM_{1-2}$, methanol, formaldehyde and TOX), with a high separation efficiency.

3. The separation of the catalyst is simple, thereby realizing recycling of the catalyst.

DESCRIPTION OF DRAWING

FIG. 1 is a flow chart of the process for preparing polyoxymethylene dimethyl ethers by an acetalation reaction of formaldehyde and methanol. This FIGURE is only a schematic flow chart for illustration of the invention, and therefore, only necessary apparatuses for explaining the process are indicated, and other indispensable devices, such as meters, gas affluxing apparatuses, pumps, valves, intermediate tanks, etc. are omitted.

SPECIFIC EMBODIMENTS

The content of the invention is further illustrated with the aid of the drawing.

(1) When starting-up or supplementing a catalyst, a catalyst of ionic liquid IL I is metered and added into reactor R1 from a catalyst storage tank V2 via line 2; and a catalyst of ionic liquid IL II is metered and added into reactor R2 from a catalyst storage tank V1 via line 1.

(2) Formaldehyde polymerization reaction-rectification: the whole reaction system is under minute negative-pressure or normal pressure. A starting material of concentrated formaldehyde in storage tank V3 is metered and flows continuously into formaldehyde polymerization reactor R1 via line 3 to perform a polymerization reaction for producing trioxymethylene under the catalysis of the ionic liquid IL I, wherein the reaction temperature is controlled to be 95-105° C. The reaction liquid discharged from the bottom of reactor R1 is introduced into a reboiler V5 via line 6 by pump P1, and then is directed back to reactor R1 via line 7. The reactor and the reboiler are connected circularly, and the reaction liquid is circulated in the reactor and the reboiler. The gas in the reactor enters a rectification tower V4 via line 4 from the top of reactor R1, and a gas-liquid separation is carried out in rectification tower V4. An azeotrope of trioxymethylene, formaldehyde and water is collected at the top of the rectification tower, and then enters a gas condenser V6 via line 8, and after condensation, enters acetalation reactor R2 via line 9. The liquid is collected at the bottom of the rectification tower and then directed to reactor R1 via line 5.

(3) Acetalation reaction: the whole system is replaced with $N_2$ or other inert gases, and the oxygen content in the system is below 10 ppm according to a test of the discharged tail gas. A starting material of a mixture of trioxymethylene, formaldehyde and water via line 9, methanol in storage tank V7 via line 10, a recycled light component b1 via line 14 and the recycled catalyst solution via line 12 are metered by a fluid mass rate meter (not shown) and flow continuously into acetalation reactor R2, respectively. $N_2$ is purified by a purifying unit, and then metered and introduced into reactor R2 via line 18. An acetalation reaction is carried out under the catalysis of the ionic liquid IL II, wherein the reaction temperature is 115-120° C. and the reaction pressure is 1.0-3.0 MPa. The reaction liquid discharged from the bottom of reactor R2 comprises the catalyst, $DMM_{1-6}$, water, and unreacted methanol, formaldehyde and trioxymethylene.

(4) Separation of the catalyst: the reactor effluent from the acetalation reaction zone is transported from reactor R2 to a rectification tower V8 via line 11, and a gas-liquid separation is carried out in rectification tower V8. The separated gas phase comprises $DMM_{1-6}$, water, and unreacted methanol, formaldehyde and trioxymethylene, which is cooled via line 13 and directed to a film evaporator V9. The liquid phase comprises the catalyst IL II and $DMM_{>6}$, which is directed back to the acetalation reaction system via line 12.

(5) Separation of the product: the gas phase separated from the top of rectification tower V8 is cooled via line 13 and directed to film evaporator V9. The separated gas phase comprises $DMM_{1-2}$, a part of water, and unreacted methanol, formaldehyde and trioxymethylene, which is cooled via line 14 and directed back to the acetalation reaction system. The separated liquid phase comprises $DMM_{3-6}$ and water, which is directed to a phase separator V10 via line 15. In phase separator V10, the lower organic phase comprises products of $DMM_{3-6}$, which is directed to a product storage tank V11 via line 16; and the upper water phase is transported to a storage tank V12 via line 17.

Examples of the catalysts used in the invention are shown below:

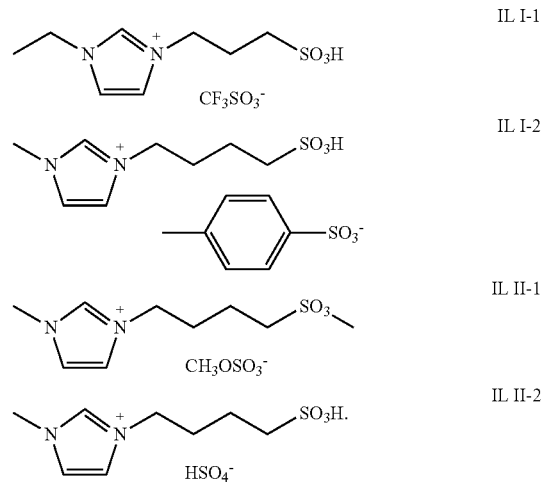

The pressures used herein are all gauge pressures.

EXAMPLE 1

In the reaction process shown in FIG. 1, the volume of reactor R1 was 1 L. Reactor R1 and the reboiler were connected circularly, and a reaction liquid was circulated in the reactor and the reboiler. Reactor R2 had a volume of 100 ml, which was equipped with a speed-adjustable electromagnetic stirrer and an oil bath jacket for heating.

The air in the system was replaced by purging with high purity nitrogen gas. To reactor R1, 150 g of a catalyst of ionic liquid IL I-1 was added continuously in 5 h, and at the same time, an aqueous formaldehyde solution with a concentration of 50 wt % was added at a feeding speed of 120 mL/h. The reaction temperature in reactor R1 was controlled to 98-100° C. The polymerization of formaldehyde produced trioxymethylene. The gas in the reactor entered a rectification tower. An azeotrope of trioxymethylene, formaldehyde and water was evaporated out of the top the tower at an overhead temperature of 92-96° C., and after condensation, entered acetalation reactor R2. Samples were taken at regular time intervals for quantitative analysis by a gas chromatograph.

To reactor R2, a catalyst of ionic liquid IL II-1 was added at a feeding speed of 7.0 g/h. The feeding was stopped when the catalyst solution began to circulate. The concentration of the catalyst was controlled to be not lower than 4 wt %. The mixture of trioxymethylene, formaldehyde and water (from the above rectification tower) and a starting material of methanol with a purity of 99% were added at feeding speeds of 120 mL/h and 48 mL/h, respectively. The operating condition of reactor R2 was controlled to be 115-120° C. and 1.0-2.0 MPa. The reaction liquid was directed to a rectification tower V8 and separated into a light component a1 ($DMM_{1-6}$, water, and unreacted methanol, formaldehyde and trioxymethylene) and a heavy component at 20-250° C. and −0.02–−0.06 MPa. The heavy component was returned to the acetalation reaction system. The light component a1 was directed into a film evaporator V9 and separated into a light component b1 and a liquid phase at 80-95° C. and −0.02 MPa. The light component b1 comprising $DMM_{1-2}$, a part of water, and unreacted methanol, formaldehyde and trioxymethylene was returned to the acetalation reaction system. The separated liquid phase was received into phase separator V10 and layers separated at 40-60° C. The top layer was water phase. The lower layer was products of $DMM_{3-6}$, which was transported to product storage tank V11. Samples were taken from the products and the light component at regular time intervals for quantitative analysis by a gas chromatograph. The reaction was continued for 100 h with test results shown in Table 1. In Table 1, all of the flow rates and compositions of substances were average values over the operation of 100 h.

TABLE 1

| | Discharging Rate | Product Distribution (%) | | | $CH_3O(CH_2O)_nCH_3$ with different n values | | | | | |
|---|---|---|---|---|---|---|---|---|---|---|
| Analysis Items | mL/h | Methanol | Formaldehyde | Trioxymethylene | 1 | 2 | 3 | 4 | 5 | 6 |
| Azeotrope of trioxymethylene-formaldehyde-water | 120 | 0.2 | 18.5 | 31.3 | 0 | 0 | 0 | 0 | 0 | 0 |
| Light Component b1 | 58 | 15.3 | 7.6 | 6.4 | 37.4 | 31.7 | 1.6 | 0 | 0 | 0 |
| Product | 95 | 1.2 | 0.8 | 0 | 0 | 0.01 | 38.4 | 36.9 | 17.2 | 5.5 |

EXAMPLE 2

The reaction was continued for 100 hours in the same manner as Example 1, with the exception of adding an ionic liquid IL I-2 as a catalyst to reactor R1 and adding an ionic liquid IL II-2 as a catalyst to reactor R2. The average values of the flow rates and compositions of substances are shown in Table 2.

TABLE 2

| | Discharging Rate | Product Distribution (%) | | | $CH_3O(CH_2O)_nCH_3$ with different n values | | | | | |
|---|---|---|---|---|---|---|---|---|---|---|
| Analysis Items | mL/h | Methanol | Formaldehyde | Trioxymethylene | 1 | 2 | 3 | 4 | 5 | 6 |
| Azeotrope of trioxymethylene-formaldehyde-water | 120 | 0.1 | 20.1 | 29.8 | 0 | 0 | 0 | 0 | 0 | 0 |
| Light Component b1 | 58 | 12.9 | 9.3 | 6.0 | 38.8 | 31.4 | 1.6 | 0 | 0 | 0 |
| Product | 91 | 1.8 | 0.9 | 0 | 0 | 0.2 | 37.4 | 35.9 | 19.2 | 4.6 |

What is claimed:

1. A method for preparing polyoxymethylene dimethyl ethers by acetalation reaction of formaldehyde and methanol comprising:
   A, in a formaldehyde polymerization reaction-rectification zone including a reaction-rectification device and a gas condenser, carrying out a continuous polymerization reaction by using an acidic ionic liquid IL I as a catalyst and an aqueous formaldehyde solution as a starting material, and passing the polymerization product through the rectification device and the gas condenser;
   B, in an acetalation reaction zone, in a single-stage or multi-stage stirred tank reactor, performing a continuous acetalation reaction between the condensate from the gas condenser in A and methanol by using an acidic ionic liquid IL II as a catalyst;
   C, in a separation zone including a single-stage or multi-stage rectification tower, a film evaporator and a phase separator connected in series, allowing the reactor effluent from the above acetalation reaction zone to drop in pressure, and flow into the rectification tower to be evaporated and condensed so as to be separated into two streams, one of a gaseous light component a1 and one of a liquid recycling catalyst; directing the recycling catalyst back to the acetalation reactor; allowing the light component a1 to flow into the film evaporator to be separated into a gaseous light component b1 comprising $DMM_{1-2}$, formaldehyde, methanol, trioxymethylene and a part of water, and a liquid phase; and allowing the separated liquid phase to flow into the phase separator to be separated into two streams, one of a product phase of $DMM_{3-6}$ and one of an aqueous phase.

2. The method according to claim 1, wherein in A, the aqueous formaldehyde solution as the starting material is 50-60 wt %.

3. The method according to claim 1, wherein in A, the polymerization reaction in the formaldehyde polymerization reaction-rectification zone is carried out at 80-120° C. and −1.0-0.1 MPa.

4. The method according to claim 1, wherein the acidic ionic liquid IL I used in A comprises a cation portion which is at least one selected from the group consisting of cations of quaternary ammoniums, cations of quaternary phosphines, cations of imidazoles, cations of pyridines and cations of heterocycles, and an anion portion which is at least one selected from the group consisting of p-toluenesulfonate, trifluoromethyl sulfonate, methyl sulfonate, hydrosulfate, and trifluoroacetate.

5. The method according to claim 1, wherein in B, the acetalation reaction is carried out at 100-130° C. and 0.5-5.0 MPa.

6. The method according to claim 1, wherein the acidic ionic liquid IL II used in B comprises a cation portion which is at least one selected from the group consisting of cations of quaternary ammoniums, cations of quaternary phosphines, cations of imidazoles, cations of pyridines and cations of heterocycles, and an anion portion which is at least one selected from the group consisting of p-toluenesulfonate, trifluoromethyl sulfonate, methyl sulfonate, methoxy sulfonate, hydrosulfate, and trifluoroacetate.

7. The method according to claim 1, wherein in C, the treatment in the rectification tower is carried out under a protection of nitrogen gas.

8. The method according to claim 1, characterized in that in C, the treatment in the film evaporator is carried out under a protection of nitrogen gas.

9. The method according to claim 1, wherein the acidic ionic liquid IL I used in A comprises a cation portion selected from cations of imidazoles, and an anion portion selected from toluenesulfonate, trifluoromethyl sulfonate and hydrosulfate.

10. The method according to claim 1, wherein in the formaldehyde polymerization reaction-rectification zone in A, the catalyst of acidic ionic liquid IL I accounts for 1-10 wt % of all the starting materials.

11. The method according to claim 1, wherein the formaldehyde polymerization reaction-rectification zone in A has a reaction temperature of 95-105° C., a pressure of −0.1 MPa −0.1 MPa, and a reaction residence time of 5-15 h.

12. The method according to claim 1, wherein in the formaldehyde polymerization reaction-rectification zone in A, the rectification tower has a bottom temperature of 90-98° C. and a overhead temperature of 92-96° C.; the rectification tower is packed with a structured packing of stainless steel and has a tray number of 10-20; and the material of the reactor is 316L stainless steel.

13. The method according to claim 1, wherein in the acetalation reaction zone in B, the starting material which is the condensate from the gas condenser in A is a mixture of trioxymethylene, formaldehyde and water, wherein the ratio of the total moles of formaldehyde and trioxymethylene to the moles of methanol which is another starting material is 0.9-3.0.

14. The method according to claim 1, wherein in B, the acidic ionic liquid IL II comprises a cation portion selected from cations of imidazoles, and an anion portion selected from methoxy sulfonate or hydrosulfate.

15. The method according to claim 1, wherein in the acetalation reaction zone in B, the catalyst of acidic ionic liquid IL II accounts for 1-5 wt % of all the starting materials.

16. The method according to claim 1, wherein in the acetalation reaction zone in B, the reaction temperature is preferably 115-120° C.; the reaction system is charged with an inert gas with a pressure of 1.0-3.0 MPa; the residence time of the reaction is 20-60 min; and
the material of the reactor is 316L stainless steel.

17. The method according to claim 1, wherein in the separation zone in C, the rectification tower is packed with a structured packing of stainless steel and has a tray number of 10-20, a pressure of −0.02--0.06 MPa and an overhead temperature of 20-260° C.

18. The method according to claim 1, wherein in the separation zone in C, the film evaporator is selected from a falling film evaporator, a scraper thin film evaporator and a scraper-less thin film evaporator, and the operating conditions thereof include an evaporation temperature of 20-100° C. and a pressure of −0.1--0.01 MPa.

19. The method according to claim 16, wherein the inert gas in nitrogen or helium gas.

20. The method according to claim 1, wherein in B, the acidic ionic liquid IL II comprises a cation selected from the group consisting of the following structural formulas:

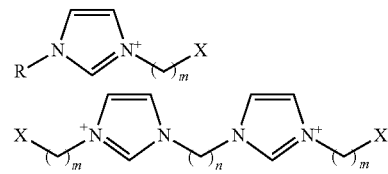

wherein, n and m are integers of 0-15; R is a straight-chain alkyl with carbon number of 1-6 or a benzene ring; and X is —$SO_3H$, COOH or —$SO_3R'$, wherein R' is $CH_3$.

21. The method according to claim 1, wherein in B, the acidic ionic liquid IL II comprises a cation selected from the group consisting of the following structural formulas:

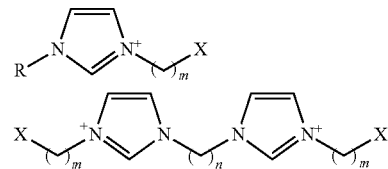

wherein, n and m are integers of 0-15; R is a straight-chain alkyl with carbon number of 1-6 or a benzene ring; and X is —$SO_3R'$, wherein R' is $CH_2CH_3$.

* * * * *